(12) United States Patent
Huang

(10) Patent No.: US 10,357,491 B2
(45) Date of Patent: *Jul. 23, 2019

(54) METHOD OF TREATING A BRAIN TUMOR

(71) Applicant: BeyondSpring Pharmaceuticals, Inc., New York, NY (US)

(72) Inventor: Lan Huang, Bronx, NY (US)

(73) Assignee: BeyondSpring Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/122,482

(22) Filed: Sep. 5, 2018

(65) Prior Publication Data

US 2019/0000841 A1   Jan. 3, 2019

Related U.S. Application Data

(63) Continuation of application No. 15/555,956, filed as application No. PCT/US2016/020396 on Mar. 2, 2016, now Pat. No. 10,076,518.

(60) Provisional application No. 62/129,623, filed on Mar. 6, 2015, provisional application No. 62/249,807, filed on Nov. 2, 2015.

(51) Int. Cl.
  *A61K 45/06* (2006.01)
  *A61P 35/00* (2006.01)
  *A61K 31/495* (2006.01)
  *A61K 31/496* (2006.01)

(52) U.S. Cl.
  CPC .......... *A61K 31/496* (2013.01); *A61K 31/495* (2013.01); *A61K 45/06* (2013.01); *A61P 35/00* (2018.01)

(58) Field of Classification Search
  None
  See application file for complete search history.

(56) References Cited

U.S. PATENT DOCUMENTS

| | | | |
|---|---|---|---|
| 5,607,934 A | 3/1997 | Tone et al. | |
| 5,733,888 A | 3/1998 | Carver et al. | |
| 5,852,018 A | 12/1998 | Bryans et al. | |
| 5,874,443 A | 2/1999 | Kiely et al. | |
| 5,886,210 A | 3/1999 | Rayle et al. | |
| 5,891,877 A | 4/1999 | Brocchini et al. | |
| 5,922,683 A | 7/1999 | Or et al. | |
| 5,939,098 A | 8/1999 | Reidenberg et al. | |
| 6,069,146 A | 5/2000 | Fenical et al. | |
| 6,350,759 B1 | 2/2002 | Casara et al. | |
| 6,358,957 B1 | 3/2002 | Fukumoto et al. | |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,583,143 B2 | 6/2003 | Haddach | |
| 6,713,480 B2 | 3/2004 | Fukumoto et al. | |
| 6,808,710 B1 | 10/2004 | Wood et al. | |
| 6,972,289 B1 | 12/2005 | Kanzaki et al. | |
| 7,026,322 B2 | 4/2006 | Hayashi et al. | |
| 7,064,201 B2 | 6/2006 | Hayashi et al. | |
| 7,488,802 B2 | 2/2009 | Collins et al. | |
| 7,629,380 B2 | 12/2009 | McMorris et al. | |
| 7,635,757 B2 | 12/2009 | Freeman et al. | |
| 7,674,903 B2 | 3/2010 | Hayashi et al. | |
| 7,700,615 B2 | 4/2010 | Edwards et al. | |
| 7,919,497 B2 | 4/2011 | Palladino et al. | |
| 7,943,743 B2 | 5/2011 | Korman et al. | |
| 7,956,058 B2 | 6/2011 | Hayashi et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 2002/0028819 A1 | 3/2002 | Teng et al. | |
| 2002/0143021 A1 | 10/2002 | Fukumoto et al. | |
| 2004/0102454 A1 | 5/2004 | Hayashi et al. | |
| 2005/0090667 A1 | 4/2005 | Hayashi et al. | |
| 2005/0197344 A1 | 9/2005 | Palladino et al. | |
| 2006/0079534 A1 | 4/2006 | Kanzaki et al. | |
| 2006/0167010 A1 | 7/2006 | Hayashi et al. | |
| 2006/0217553 A1 | 9/2006 | Hayashi et al. | |
| 2006/0223822 A1 | 10/2006 | Hayashi et al. | |
| 2006/0223823 A1 | 10/2006 | Hayashi et al. | |
| 2007/0078138 A1 | 4/2007 | Palladino et al. | |
| 2008/0221122 A1 | 9/2008 | Palladino et al. | |
| 2009/0317368 A1 | 12/2009 | Chen | |
| 2012/0277251 A1 | 11/2012 | Palladino et al. | |
| 2016/0250209 A1 | 9/2016 | Huang | |
| 2018/0028531 A1 | 2/2018 | Huang et al. | |
| 2018/0036304 A1 | 2/2018 | Huang | |
| 2018/0042921 A1 | 2/2018 | Huang | |

FOREIGN PATENT DOCUMENTS

| | | |
|---|---|---|
| CA | 2403790 A1 | 7/2001 |
| EP | 0655060 B1 | 1/1998 |
| EP | 1264831 A1 | 12/2002 |
| GB | 2143823 | 2/1985 |

(Continued)

OTHER PUBLICATIONS

Abels, Christoph, Targeting of the Vascular System of Solid Tumours by Photodynamic Therapy (PDT), Photochem Photobiol Sci., (Mar. 2004) 3: 765-771.

Abstracts of the 1999 Joint Chubu and Kansai Branch Conference and Symposia of Japan Society for Bioscience, Biotechnology, and Agrochemistry, (1999) p. 48.

Aggarwal et al., Antiangiogenic agents in the management of non-small cell lung cancer: Where do we stand now and where are we headed? Cancer Biology & Therapy (2012), 13(5), 247-263.

Ahmed et al. "A new rapid and simple non-radioactive assay to monitor and determine the proliferation of lymphocytes: an alternative to [$^3$H]thymidine incorporation assay." J. Immunol. Methods. 170, 211-224 (1994).

Akerlund et al., "Diketopiperazine-Based Polymers from Common Amino Acids," Journal of Applied Polymer Science, (2000) 78 (12), 2213-2218.

(Continued)

*Primary Examiner* — Brian J Davis

(74) *Attorney, Agent, or Firm* — Knobbe, Martens, Olson & Bear, LLP

(57) ABSTRACT

Disclosed herein are methods of treating a brain tumor by administering Plinabulin. Some embodiments relate to treatment of glioblastoma multiforme by administering Plinabulin.

20 Claims, 3 Drawing Sheets

(56) References Cited

FOREIGN PATENT DOCUMENTS

| | | |
|---|---|---|
| JP | 5009164 | 1/1993 |
| JP | 10130266 | 5/1998 |
| JP | 2002-507612 A | 3/2002 |
| JP | 2007-520565 A | 7/2007 |
| JP | 2018-5201178 A | 7/2018 |
| JP | 6411523 | 10/2018 |
| KR | 10-2018-0027563 A | 3/2018 |
| RU | 2011 148 945 A | 4/2010 |
| RU | 2662298 C2 | 7/2018 |
| WO | WO 87/05297 | 9/1987 |
| WO | WO 1995/21832 | 8/1995 |
| WO | WO 1996/20190 | 7/1996 |
| WO | WO 1999/38844 | 8/1999 |
| WO | WO 1999/048889 | 9/1999 |
| WO | WO 2001/053290 | 7/2001 |
| WO | WO 2004/054498 | 7/2004 |
| WO | WO 2005/077940 | 8/2005 |
| WO | WO 2009/089260 A2 | 7/2009 |
| WO | WO 2011/066389 A1 | 6/2011 |
| WO | WO 2011/146382 A1 | 11/2011 |
| WO | WO 2011/151423 A1 | 12/2011 |
| WO | WO 2012/014549 | 2/2012 |
| WO | WO 2012/035436 A1 | 3/2012 |
| WO | WO 2012/145493 A1 | 10/2012 |
| WO | WO 2014/160183 | 10/2014 |
| WO | WO 2015/051543 A1 | 4/2015 |
| WO | WO 2015/160641 A2 | 10/2015 |
| WO | WO 2016/130839 A1 | 8/2016 |
| WO | WO 2016/144635 A1 | 9/2016 |
| WO | WO 2016/144636 A1 | 9/2016 |
| WO | WO 2017/011399 A1 | 1/2017 |
| WO | WO 2017/139231 A1 | 8/2017 |
| WO | WO 2017/214052 A1 | 12/2017 |
| WO | WO 2018/129381 A1 | 7/2018 |
| WO | WO 2018/144764 A1 | 8/2018 |
| WO | WO 2018/169887 A1 | 9/2018 |

OTHER PUBLICATIONS

Algaier et al. "The effects of dimethyl sulfoxide on the kinetics of tubulin assembly." Biochim. Biophys. Acta. 954, 235-43 (1988).
Ali et al. "Toxicity of echinulin from Aspergillus chevalieri in rabbits." Toxicology Letters. (1989) 48: 235-41.
Asahina, T., "Spectrochemical Study of Amino-acid Anhydrides," Bulletin of the Chemical Society of Japan, (1930) 5, 354-365.
Augustin, M. "Die Umsetzung des 2,5-Diketopiperazins mit Aldehyden und Nitrosoverbindungen" Journal für Praktische Chemie, (1966) 32(4), 158-166.
Bankowska et al., Derivatives of 1,2,3-triazole. Potential drugs?, Wiadomosci Chemiczne (2012), 66(11-12), 993-1022.
Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.
Bertelsen et al., Vascular effects of plinabulin (NPI-2358) and the influence on tumour response when given alone or combined with radiation, International Journal of Radiation Biology (2011),87(11), 1126-1134.
Bertino J., et al., "Principles of Cancer Therapy." Cecil Textbook of Medicine. Eds. Lee Goldman, et al. 21nd ed., (2000), Chapter 198, pp. 1060-1074.
Bond et al. "The Synthesis of Viridamine, a Penicillium Viridicatum Mycotoxin." Synthetic Commun. 19 (13&14), 2551-2566 (1989).
Borisy, G.G. "A Rapid Method for Quantitative Determination of Microtubule Protein using DEAE-Cellulose Filters." Anal. Biochem. 50, 373-385 (1972).
Burtles, Sally, "Transition from Preclinical to first-in-man Phase", Expert Scientific Group on Phase One Clinical Trials Final Report, Presentation Jun. 19, 2006, pp. 35-38.
Cai, Sui X., "Small Molecule Vascular Disrupting Agents: Potential New Drugs for Cancer Treatment", Recent Pat Anticancer Drug Discov. (2007) 2(1): 79-101.
Cai, Small molecule vascular disrupting agents: potential new drugs for cancer treatment, a 2009 update, Frontiers in Anti-Cancer Drug Discovery (2010), 1, 380-427.
Chaplin et al., "Antivascular approaches to solid tumour thereapy: evaluation of tubulin binding agents", Br. J. Cancer 1996, 74 (Suppl. XXVII), S86-S88.
Cui et al. "Novel Mammalian Cell Cycle Inhibitors, Tryprostatins A, B and Other Diketopiperazines Produced by Aspergillus fumigatus." J. Antibiotics. 49(6): 527-33 (1996).
Cui et al. "Novel Mammalian Cell Cycle Inhibitors, Tryprostatins A, B and Other Diketopiperazines Produced by Aspergillus fumigatus." J. Antibiotics. 49(6), 534-40 (1996).
Dandan et al., JP 5009164, Chemical Abstract 119: 8514 (1993).
Davis et al., ZD6126: A Novel Vascular-targeting Agent That Causes Selective Destruction of Tumor Vasculature, Cancer Research (Dec. 15, 2002) 62: 7247-7253.
Dörwald, F., "Side Reactions in Organic Synthesis" Wiley-VCH Verlag GmbH & Co. KgaA, Weinheim, (2005), book cover and preface p. IX only.
Drug Approval and Licensing Procedures in Japan 2001, 2001, pp. 243-244.
Ferrer et al., Plinabulin: tubulin polymerization inhibitor vascular-disrupting agent oncolytic, Drugs of the Future (2010), 35(1), 11-15.
Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.
Frost et al., Novel Syngeneic Pseudo-orthotopic Prostate Cancer Model: Vascular, Mitotic and Apoptotic Responses to Castration, Microvasc Research (Dec. 2004) 69: 1-9.
Fukushima et al., "Biological Activities of Albonoursin," J. Antibiotics, (1973) 26:175.
Gallina et al., "Condensation of 1,4-diacetylpiperazine-2,5-dione with aldehydes", Tetrahedron 1974, 30, 667-673.
Goldani et al. "Treatment of murine pulmonary mucormycosis with SCH 42427, a broad-spectrum triazole antifungal drug", Correspondence, J Antimicrob Chemother. 33, 369-372 (1994).
Goldfarb et al., "Synthesis of β-2-thienylalanine," Izvestiya Akademii Nauk SSSR, Seriya Khimicheskaya, (1958) 98-100, as abstracted by CAPLUS.
Gordon et al. "Reductive Alkylation on a Solid Phase: Synthesis of a Piperazinedione Combinatorial Library." J. Bioorg. Med. Chem. Letters. 5, 47-50 (1995).
Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4): 1021-1025.
Gridelli et al., Vascular disrupting agents: a novel mechanism of action in the battle against non-small cell lung cancer, Oncologist (2009), 14(6), 612-620.
Gura, Trisha, "Cancer Models: Systems for Identifying New Drugs are Often Faulty", Science 7(Nov. 1997) 278(5340): 1041-1042.
Hamel, E. "Antimitotic Natural Products and Their Interactions with Tubulin." Med. Res. Rev. (1996) 16(2): 207-31.
Hartwell et al. "Checkpoints: Controls that Ensure the Order of Cell Cycle Events." Science. 246, 629-34 (1989).
Hayakawa, Structure-activity relationship analysis, Gan to Kagaku Ryoho (2004), 31(4), 526-528.
Hayashi et al., "Total Synthesis of Anti-microtubule Diketopiperazine Derivatives: Phenylahistin and Aurantiamine," J. Org. Chem., (2000) 65: 8402-8405.
Hayashi et al., Small peptide-based medicinal chemistry for intractable disease, Peptide Science (2009), vol. Date 2008, 45th, 139-140.
Hayashi et al., Medicinal chemistry and chemical biology of diketopiperazine-type antimicrotubule and vascular-disrupting agents, Chemical & Pharmaceutical Bulletin (2013), 61(9), 889-901.
Heist, R. et al. 2014 "Randomized phase 2 trial of plinabulin (NPI-2358) plus docetaxel in patients with advanced non-small cell lung cancer (NSCLC)." J. Clin. Oncol. vol. 32, No. 5s, (suppl; abstr 8054).
Helleman et al. "The International Journal of Biochemistry & Cell Biology," vol. 42, pp. 25-30 (2010).

(56) References Cited

OTHER PUBLICATIONS

Horak et al. "Structures of the Austalides A-E, Five Novel Toxic Metabolites from Aspergillus ustus." J Chem Soc Chem Commun. (1981) 1265-67.
http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).
Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.
Iwasaki, S. "Antimitotic Agents: Chemistry and Recognition of Tubulin Molecule." Med Res Rev. (1993) 13: 183-198.
Iwasaki, S. "Bioactive Natural Products Interfering with Microtubule Function." Kagaku to Seibutsu. 32(3): 153-159 (1994).
Ji et al. Tubulin Colchicine Binding Site Inhibitors as Vascular Disrupting Agents in Clinical Developments, Current Medicinal Chemistry (2015), 22(11), 1348-1360.
Johnson et al. "Kinetic Analysis of Microtubule Self-assembly in Vitro." J. Mol. Biol. 117, 1-31 (1977).
Jure-Kunkel M. et al., "Synergy between chemotherapeutic agents and CTLA-4 blockade in preclinical tumor models", Cancer Immunol. Immunother. 2013, vol. 62, pp. 1533-1545.
Kamb, Alexander, "What's wrong with our cancer models?", Nature Reviews Drug Discovery (Feb. 2005) 4: 161-165.
Kanoh et al., "(−)-Phenylahistin: A New Mammalian Cell Cycle Inhibitor Produced by Aspergillus Ustus," Bioorganic & Medicinal Chemistry Letters, (1997) 7: 2847-2852.
Kanoh et al., "(−)-Phenylahistin Arrests Cells in Mitosis by Inhibiting Tubulin Polymerization," The Journal of Antibiotics, (1999) 52: 134-141.
Kanoh et al., "Antitumor Activity of Phenylahistin in Vitro and in Vivo," Bioscience Biotechnology Biochemistry, (1999) 63(6): 1130-1133.
Kanoh et al., "Synthesis and Biological Activities of Phenylahistin Derivatives," Bioorganic & Medicinal Chemistry, (1999) 7: 1451-1457.
Kanthou et al., Microtubule depolymerizing vascular disrupting agents: novel therapeutic agents for oncology and other pathologies, International Journal of Experimental Pathology(2009), 90(3), 284-294.
Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).
Kanzaki et al., "Novel Cyclic Dipeptide Dehydrogenase and Assay Method for Its Activity," Scientific Reports of the Faculty of Agriculture, Okayama University, (1999) 88: 7-11.
Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.
Kanzaki et al., "Effective Production of Dehydro Cyclic Dipeptide Albonoursin Exhibiting Pronuclear Fusion Inhibitory Activity, I. Taxonomy and Fermentation," The Journal of Antibiotics, (1999) 52: 1017-1022.
Kanzaki et al., "Effective Production of Dehydro Cyclic Dipeptide Albonoursin Exhibiting Pronuclear Fusion Inhibitory Activity, II. Biosynthetic and Bioconversion Studies," The Journal of Antibiotics, (2000) 53(1): 58-62.
Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12): 1042-1047.
Keepers et al. "Comparison of the Sulforhodamine B Protein and Tetrazolium (MTT) Assays for in vitro Chemosensitivity Testing." Eur. J. Cancer. 27, 897-900 (1991).
Kim et al. "Polymer attached cyclic peptides, tetrahedron: Asymmetry." 3(11):1421-1430 (1992).

Kingston, Tubulin-Interactive Natural Products as Anticancer Agents, Journal of Natural Products (2009), 72(3), 507-515.
Kingston, Correction to Tubulin-interactive natural products as anticancer agents, Journal of Natural Products (2011), 74(5), 1352.
Kobayashi et al., "Microtubule Assembly Regulators of Microbial Origin," Abstract of Paper Read at the 1989 Symposium on the Chemistry of Natural Products, (1989) 51.
Kola et al., "Can the pharmaceutical industry reduce attrition rates?", Nature Reviews Drug Discovery (2004) 3: 711-715.
Kondoh et al. "Effects of Tryprostatin Derivatives on Microtubule Assembly In Viro and In Situ." J. Antibiotics. 51, 801-04 (1998).
Kopple et al., "A Convenient Synthesis of 2,5-Piperazinediones1a," The Journal of Organic Chemistry, (1967) 33: 862-864.
Kreamer K., "Immune checkpoint blockade: a New Paradigm in Treating Advanced Cancer", J. Adv. Pract. Oncol., 2014, vol. 5, pp. 418-431.
Krishan, A. "Rapid Flow Cytofluorometric Analysis of Mammalian Cell Cycle by Propidium Iodide Staining." J. Cell Biol. 66, 188-193 (1975).
Küster & Koeppenhöfer, "Über eininge Pyrrolderivate," Z. Physiol, Chem., (1927) 172:126-137.
Kupchan et al. "Steganacin and Steganangin, Novel Antileukemic Lignan Lactones from Steganotaenia araliacea 1-3." J. Am. Chem. Soc. (1973) 95(4): 1335-36.
Lacey et al. "Interaction of Phomopsin A and Related Compounds with Purified Sheep Brain Tubulin." Biochem. Pharmacol. 36, 2133-38 (1987).
Laemmli, U.K. "Cleavage of Structural Proteins during the Assembly of the Head of Bacteriophage T4." Nature. 227, 680-85 (1970).
Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (and how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., Colchicine site inhibitors of microtubule integrity as vascular disrupting agents, Drug Development Research (2008), 69(6), 352-358.
Li, Y., et al. "Interaction of marine toxin dolastatin 10 with porcine brain tubulin: competitive inhibition of rhizoxin and phomopsin A binding." Chem. Biol. Interact. 93, 175-83 (1994).
Liwo et al. "Origin of the Ring-Ring Interaction in Cyclic Dipeptides Incorporating an Aromatic Amino Acid." Tetrahedron Lett. 26, 1873-1876 (1985).
Luduena, R.F. "Contrasting Roles of Tau and Microtubule-associated Protein 2 in the Vinblastine-induced Aggregation of Brain Tubulin." J. Biol. Chem. 259:12890-98 (1984).
Mahindroo et al., "Antitubulin Agents for the Treatment of Cancer—A Medicinal Chemistry Update", Expert Opin. Ther. Patents (2006) 16(5): 647-691.
Millward et al., Phase 1 study of the novel vascular disrupting agent plinabulin (NPI-2358) and docetaxel, Investigational New Drugs (2012), 30(3), 1065-1073.
Mita et al., Phase 1 First-in-Human Trial of the Vascular Disrupting Agent Plinabulin(NPI-2358) in Patients with Solid Tumors or Lymphomas, Clinical Cancer Research (2010), 16(23), 5892-5899.
Mita et al., Randomized Phase 2 Study of Docetaxel +/− Plinabulin (NPI-2358) in Patients with Non-Small Cell Lung Cancer (NSCLC) Mol Cancer Ther 8 Suppl. (Abstr C30) (2009) 2 pages.
Mita et al., Randomized Phase 2 Study of Docetaxel +/− Plinabulin (NPI-2358) in Patients with Non-Small Cell Lung Cancer (NSCLC), Poster Presentation at ACS Annual '10 Meeting (Jun. 4-8, 2010) 1 page.
Neidle, Stephen, ed., Cancer Drug Design and Discovery, 9th Edition, Elsevier/Academic Press, (2008) Chapter 18, pp. 427-431.
Nema et al., Excipients and Their Role in Approved Injectable Products: Current Usage and Future Directions, PDA J Pharm Sci and Tech 2011, 65 287-332.
Nicholson et al., NPI-2358 is a tubulin-depolymerizing agent: in-vitro evidence for activity as a tumor vascular-disrupting agent, Anti-Cancer Drugs (2005), vol. Date 2006, 17(1), 25-31.

(56) References Cited

OTHER PUBLICATIONS

Niemann et al, "The Synthesis of the Three Isomeric dl-β-Pyridylalanines" Journal of the American Chemical Society, (1942) 64(7):1678-1682.
Nihei et al., "Evaluation of antivascular and antimitotic effects of tubulin binding agents in solid tumor therapy", Jpn. J. Cancer. Res. 1999, 90, 1387-1395.
Nitecki et al., "A Simple Route to Sterically Pure Diketopiperazines1," The Journal of Organic Chemistry, (1968) 33:864-866.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.
Prior, I. et al. 2012 "A Comprehensive Survey of Ras Mutations in Cancer" Cancer Res. vol. 72, No. 10, pp. 24570-2467.
Roberge et al. "Antitumor Drug Fostriecin Inhibits the Mitotic Entry Checkpoint and Protein Phospatases 1 and 2A." Cancer Res. 54, 6115-21 (1994).
Roberts et al, "Trends in the Risks and Benefits to Patients with Cancer Participating in Phase 12 Clinical Trials", JAMA (2004) 292(17): 2130-2140.
Rowinsky et al. "Taxol: A Novel Investigational Antimicrotubule Agent." J. Natl. Cancer Inst. 82(15): 1247-59 (1990).
Rowinsky et al, "The clinical pharmacology and use of antimicrotubule agents in cancer chemotherapeutics", Pharmacol. Ther. 1991, 52, 35-84.
Sackett, D.L. "Podophyllotoxin, Steganacin and Combretastatin: Natural Products that Bind at the Colchicine Site of Tubulin." Pharmacol. Ther. (1993) 59: 163-228.
Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.
Sezaki et al., "Drug Delivery Systems", Drug Development, (Jul. 1989) 13: 116, Table 2. 29.
Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.
Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.
Sherline et al. "Binding of Colchicine to Purifiied Microtubule Protein." J. Biol. Chem. 250, 5481-86 (1975).
Shi, Q et al, "Recent progress in the development of tubulin inhibitors as antimitotic antitumor agents", Curr. Pharm. Des. 1998, 4, 219-248.
Singh et al., A novel vascular disrupting agent plinabulin triggers JNK-mediated apoptosis and inhibits angiogenesis in multiple myeloma cells, Blood (2011), 117(21), 5692-5700.
Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.
Smedsgaard et al. "Using direct electrospray mass spectrometry in taxonomy and secondary metabolite profiling of crude fungal extracts." J. Microbiol. Meth. (1996) 25: 5-17.
Sölter et al., Barettin, Revisited? Tetrahed Lttrs. (Mar. 2002) 43: 3385-3386.
Spear et al., Vascular disrupting agents (VDA) in oncology: advancing towards new therapeutic paradigms in the clinic, Current Drug Targets (2011), 12(14), 2009-2015.
Stein, J., ed. "Internal Medicine," Fourth Edition, Mosby-Year Book, Inc., (1994), Chapters 71-72, pp. 699-729.
Steyn, P.S. "The Structures of Five Diketopiperazines from Aspergillus Ustus." Tetrahedron. 29, 107-120 (1973).
Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).
Takahashi et al. "Rhizoxin binding to tubulin at the maytansine-binding site." Biochim. Biophys. Acta. 926, 215-23 (1987).
Talmadge et al., Murine models to evaluate novel and conventional therapeutic strategies for cancer., Am J Pathol, 2007, vol. 170, Issue 3, pp. 793-804.
Thorpe, Philip E., "Vascular Targeting Agents as Cancer Therapeutics," Clinical Cancer Research, vol. 10, 415-427, Jan. 15, 2004,.
Tiwari et al. "A pH- and Temperature-Dependent Cycling Method that doubles the Yield of Microtubule Protein." Anal. Biochem. 215, 96-103 (1993).
Tozer et al., Tumour vascular disrupting agents: combating treatment Resistance, British Journal of Radiology (2008), 81(Spec. Iss. 1), S12-S20.
Turner et al. "Recent Advances in the Medicinal Chemistry of Antifungal Agents." Current Pharmaceutical Design. 2, 209-224 (1996).
Usui et al. "Tryprostatin A, a specific and novel inhibitor of microtubule assembly." Biochem J. 333, 543-48 (1998).
Van der Waerden, B.L., "Wirksamkeits- and Konzentrationsbestimmung durch Tierversuche." Arch Exp Pathol Pharmakol. 195, 389-412, (1940).
Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).
Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.
Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.
Weisenberg et al. "The Colchicine-Binding Protein of Mammalian Brain and its Relation to Microtubules." Biochemistry (1968) 7(12): 4466-79.
Wilt JA et al. "Anal cancer in Alaska; a retrospective study of incidence, treatment, and outcomes". Alaska Med Jul.-Sep. 2002; 44(3):56-9, 62.
Yahara et al. "Microtubule Organization of Lymphocytes and its Modulation by Patch and Cap Formation." Cell. 15, 251-259 (1978).
Yamazaki et al. "Crystal Structure and Absolute Configuration of Fumitremorgin B, a Tremorgenic Toxin from Aspergillus Fumigatus Fres." Tetrahedron Lett. 1, 27-28 (1975).
Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.
Yamazaki et al., Drug discovery study on cyclic dipeptides anticancer drugs and chemical biological development, Idenshi Igaku Mook (2012), 21(Saishin Pepuchido Gosei Gijutsu to Sono Soyaku Kenkyu eno Oyo), 260-266.
Yamori T., "A Human Cell Line Panel for Screening Anti-Cancer Drugs", Jap. J. Cancer Chemother. 24, 129-35 (1997).
Yin et al., "Human Mutations That Confer Paclitaxel Resistance," Mol. Cancer Ther. vol. 9(2), pp. 327-335 (2010).
Yokoi et al, "Neihumicin, A New Cytotoxic Antibiotic From Micromonospora Neihuensis," The Journal of Antibiotics, (Apr. 1988) 41(4):494-501.
Yoshida, M.M. Protein Nucleic Acid Enzymes. 38, 1753-1765 (1993).
Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).
Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.

(56) References Cited

OTHER PUBLICATIONS

Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1): 19-25.

Mita et al., Clinical Cancer Research (2010), vol. 16(23), pp. 1/19-19/19.

Petrillo et al., Current Pharmaceutical Design (2012), vol. 18, pp. 2702-2712.

Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.

Aviel-Ronen et al., "K-ras Mutations in Non-Small-Cell Lung Carcinoma: A Review," Clinical Lung Cancer (Jul. 2006) vol. 8, No. 1, pp. 30-38.

Brahmer et al., "Safety and Activity of Anti-PD-L1 Antibody in Patients with Advanced Cancer," N Engl J Med (2012) 366:2455-2465.

Callahan et al., "At the Bedside: CTLA-4- and PD-1-blocking antibodies in cancer immunotherapy", J Leukocyte Biol, vol. 94, Jul. 2013, pp. 41-53.

Cooper et al., "Response to BRAF Inhibition in Melanoma Is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.

Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.

Garris et al., "Successful Anti-PD-1 Cancer Immunotherapy Requires T Cell-Dendritic Cell Crosstalk Involving the Cytokines IFN-γ and IL-12," Immunity (Dec. 18, 2018) 49, pp. 1-14, e1-e7 (22 pages).

Heist et al., "Abstract C30: Phase 1/2 study of the vascular disrupting agent (VCA) plinabulin (NPI-2358) combined with docetaxel in patients with non-small cell lung cancer (NSCLC)," Mol. Cancer Ther., 2009; 8(12 Suppl):C30, 2 pages.

Heist et al., "Randomized Phase 2 Trial of Plinabulin (NPI-2358) Plus Docetaxel in Patients with Advanced Non-Small Lung Cancer (NSCLC)," 2014 ASCO Annual Meeting . . . (abstr 8054) Poster Presentation. Retrieved from the internet Jul. 17, 2017: <http://meetinglibrary.asco.org/record/92548/poster>.

Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.

Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.

Lyman et al., "Risk Models for Predicting Chemotherapy-Induced Neutropenia," The Oncologist (2005) 10:427-437.

Mita et al., "Phase II study of docetaxel with or without plinabulin (NPI-2358) in patients with non-small cell lung cancer (NSCLC)", J. Clin. Oncol., 2010, vol. 28, No. 15 supplement. Abstract 7592, 2 pages.

Mitsudomi et al., "Mutations of ras genes distinguish a subset of non-small-cell lung cancer cell lines from small-cell lung cancer cell lines," Oncogene (Aug. 1991) vol. 6, No. 8, pp. 1352-1362.

Mohanlal et al., "The plinabulin/docetaxel combination to mitigate the known safety concerns of docetaxel," J Clin Oncol (2016) 34(15_suppl), Abstract e20595.

Ott et al., "CTLA-4 and PD-1/PD-L1 Blockade: New Immunotherapeutic Modalities with Durable Clinical Benefit in Melanoma Patients," Clin. Cancer Res. (Oct. 1, 2013) 19(19):5300-5309.

Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.

Perez, Edith A., "Paclitaxel in Breast Cancer," The Oncologist, 1998, vol. 3, pp. 373-389.

Rhodes, John, "Section Review: Biologicals & Immunologicals: Therapeutic potential of Schiff base-forming drugs," Expert Opinion on Investigational Drugs (1996) vol. 5, Issue 3, pp. 257-268.

Rozali et al., "Programmed Death Ligand 2 in Cancer-Induced Immune Suppression," Clinical and Developmental Immunology (2012) Article ID 656340, pp. 1-8.

Stenehjem et al., "PDI/PDLI inhibitors for the treatment of advanced urothelial bladder cancer," OncoTargets and Therapy (2018) 11:5973-5989.

Wang, Y. et al, "Structures of a diverse set of colchicine binding site inhibitors in complex with tubulin provide a rationale for drug discovery." FEBS Journal (2016) 283, 102-111.

Yeh et al., "A Phase 1 Trial Combining Plinabulin and Nivolumab for Metastatic Squamous NSCLC," International Association for the Study of Lung Cancer, Journal of Thoracic Oncology (2015) Abstract 602, P2.01-087.

International Search Report and Written Opinion dated May 19, 2016 for PCT/US2016/020396.

Extended European Search Report dated Jul. 2, 2018 for EP 16 762 150.7.

Australian Examination Report No. 1 dated Feb. 8, 2019 for Australian Application No. 2013402794.

New Zealand First Examination Report dated Jan. 12, 2018 for New Zealand Application No. NZ 735213.

New Zealand First Examination Report dated Sep. 3, 2018 for New Zealand Application No. NZ 735213.

New Zealand First Examination Report dated Feb. 8, 2019 for New Zealand Application No. NZ 735213.

South African Notice of Allowance dated Jul. 27, 2018 for South African Application No. ZA2017/06035.

METHOD OF TREATING A BRAIN TUMOR

INCORPORATION BY REFERENCE TO ANY PRIORITY APPLICATIONS

This application is a continuation of U.S. application Ser. No. 15/555,956 filed on Sep. 5, 2017, which is the U.S. National Phase of International Application No. PCT/US2016/020396 entitled METHOD OF TREATING A BRAIN TUMOR, filed Mar. 2, 2016 and published on Sep. 15, 2016 as WO 2016/144636, which claims the benefit of U.S. Provisional Application No. 62/129,623, filed Mar. 6, 2015, and U.S. Provisional Application No. 62/249,807, filed Nov. 2, 2015, the disclosure of which are incorporated herein by reference in their entireties.

BACKGROUND

Field

The present invention relates to the field of chemistry and medicine. More particularly, the present invention relates to method of treating a brain tumor using Plinabulin.

Description of the Related Art

Cancers of the brain and nervous system are among the most difficult to treat. Prognosis for patients with these cancers depends on the type and location of the tumor as well as its stage of development. For many types of brain cancer, average life expectancy after symptom onset may be months or a year or two. Treatment consists primarily of surgical removal and radiation therapy. Chemotherapy is also used, but the range of suitable chemotherapeutic agents is limited, perhaps because most therapeutic agents do not penetrate the blood-brain barrier adequately to treat brain tumors. Using known chemotherapeutics along with surgery and radiation rarely extends survival much beyond that produced by surgery and radiation alone. Thus improved therapeutic options are needed for brain tumors, and this condition has a dire unmet medical need.

Glioblastoma multiforme (GBM) is the most common adult primary brain tumor and is notorious for its lethality and lack of responsiveness to current treatment approaches. There have been no substantial improvements in treatment options in recent years, and minimal improvements in the survival prospects for patients with GBM. For GBM, average life expectancy after symptom onset is around 6-12 month. In addition, there are no approved drugs for treating metastatic brain tumor, which has an average life expectancy after symptom onset at 4-6 months. Thus there remains an urgent need for improved treatments for cancers of the brain.

SUMMARY

Some embodiments relate to a method of treating a brain tumor comprising administering an effective amount of Plinabulin to a subject in need thereof.

Some embodiments relate to a method of inhibiting proliferation of brain tumor cell, comprising contacting the brain tumor cell with Plinabulin.

Some embodiments relate to a method of inducing apoptosis in brain tumor cell, comprising contacting the brain tumor cell with Plinabulin.

Some embodiments relate to a method of inhibiting progression of brain tumor, comprising administering an effective amount of Plinabulin to a subject in need thereof.

BRIEF DESCRIPTION OF THE DRAWINGS

FIG. 1a shows T2 MRI images of a human GBM that display peritumoral edema; and FIG. 1b shows T2 MRI images of mouse GBM that display peritumoral edema; FIG. 1c shows human micrograph images of H&E stains of a GBM showing hallmark pseudopalisading necrosis and microvascular proliferation; FIG. 1d shows mouse micrograph images of H&E stains of a GBM showing hallmark pseudopalisading necrosis and microvascular proliferation.

FIG. 2A shows tumor size in mice with PDGF-induced gliomas treated with vehicle, temozolomide or fractionated radiation; and FIG. 2B shows survival of mice with PDGF-induced gliomas treated with vehicle, temozolomide or fractionated radiation.

DETAILED DESCRIPTION OF THE PREFERRED EMBODIMENT

Figure 1:
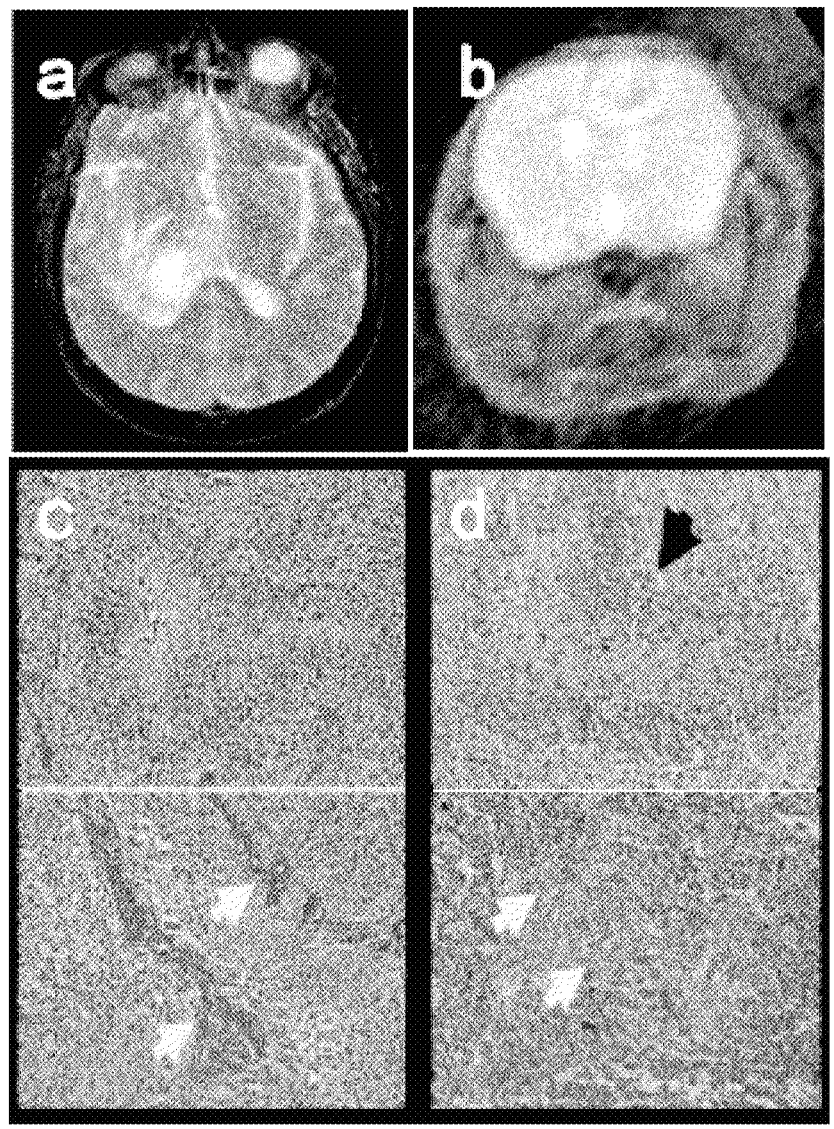
FIGS. 1a-1d show the proneural genetically engineered murine model (GEMM) of glioblastoma (GBM) that mimics human pathology.

Plinabulin, (3Z,6Z)-3-Benzylidene-6-{[5-(2-methyl-2-propanyl)-1H-imidazol-4-yl]methylene}-2,5-piperazin-edione, is a synthetic analog of the natural compound phenylahistin. Plinabulin can be readily prepared according to methods and procedures detailed in U.S. Pat. Nos. 7,064,201 and 7,919,497, which are incorporated herein by reference in their entireties. Some embodiments relate to using Plinabulin to treat brain cancer, including but are not limited to metastatic brain tumor, anaplastic astrocytoma, glioblastoma multiforme, oligodendroglioma, ependymomas, and mixed glioma. Some embodiments relate to using Plinabulin to inhibit proliferation of brain tumor cells using Plinabulin. Some embodiments relate to using Plinabulin to induce apoptosis in brain tumor cells using Plinabulin. Some embodiments relate to using Plinabulin to inhibit progression of brain tumors. Some embodiments relate to using Plinabulin in combination with an additional therapeutic agent or radiation to inhibit progression of brain tumors.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

In some embodiments, the composition can further include one or more pharmaceutically acceptable diluents. In some embodiments, the pharmaceutically acceptable diluent can include Kolliphor® (Polyethylene glycol (15)-hydroxystearate). In some embodiments, the pharmaceutically acceptable diluent can include propylene glycol. In some embodiments, the pharmaceutically acceptable diluents can include kolliphor and propylene glycol. In some embodiments, the pharmaceutically acceptable diluents can include kolliphor and propylene glycol, wherein the kolliphor is about 40% by weight and propylene glycol is about 60% by weight based on the total weight of the diluents. In some embodiments, the composition can further include one or more other pharmaceutically acceptable excipients.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of Plinabulin or pharmaceutically acceptable salts thereof; and (b) a pharmaceutically acceptable carrier, diluent, excipient or combination thereof.

Other embodiments include co-administering Plinabulin and an additional therapeutic agent in separate compositions or the same composition. Thus, some embodiments include a first pharmaceutical compositions comprising: (a) a safe and therapeutically effective amount of Plinabulin or pharmaceutically acceptable salts thereof and (b) a pharmaceutically acceptable carrier, diluent, excipient or combination thereof; and a second pharmaceutical composition comprising: (a) a safe and therapeutically effective amount of an additional therapeutic agent and (b) a pharmaceutically acceptable carrier, diluent, excipient or combination thereof. Some embodiments include a pharmaceutical composition comprising: (a) a safe and therapeutically effective amount of Plinabulin or pharmaceutically acceptable salts thereof; (b) a safe and therapeutically effective amount of an additional therapeutic agent; and (c) a pharmaceutically acceptable carrier, diluent, excipient or combination thereof.

Administration of the pharmaceutical compositions described herein can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, or intraocularly. Oral and parenteral administrations are customary in treating the indications that are the subject of the preferred embodiments.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The compositions described herein are preferably provided in unit dosage form. As used herein, a "unit dosage form" is a composition containing an amount of a compound or composition that is suitable for administration to an animal, preferably a mammalian subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, sublingual, buccal, nasal, rectal, topical (including transdermal and intradermal), ocular, intracerebral, intracranial, intrathecal, intraarterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g., liquid gel capsule and solid gel capsule), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, sucrose, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80 Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium (EDTA), although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan. In some embodiments, a single dose of Plinabulin or other therapeutic agent may be from about 5 mg/m$^2$ to about 150 mg/m$^2$ of body surface area, from about 5 mg/m$^2$ to about 100 mg/m$^2$ of body surface area, from about 10 mg/m$^2$ to about 100 mg/m$^2$ of body surface area, from about 10 mg/m$^2$ to about 80 mg/m$^2$ of body surface area, from about 10 mg/m$^2$ to about 50 mg/m$^2$ of body surface area, from about 10 mg/m$^2$ to about 40 mg/m$^2$ of body surface area, from about 10 mg/m$^2$ to about 30 mg/m$^2$ of body surface area, from about 13.5 mg/m$^2$ to about 100 mg/m$^2$ of body surface area, from about 13.5 mg/m$^2$ to about 80 mg/m$^2$ of body surface area, from about 13.5 mg/m$^2$ to about 50 mg/m$^2$ of body surface area, from about 13.5 mg/m$^2$ to about 40 mg/m$^2$ of body surface area, from about 13.5 mg/m$^2$ to about 30 mg/m$^2$ of body surface area, from about 15 mg/m$^2$ to about 80 mg/m$^2$ of body surface area, from about 15 mg/m$^2$ to about 50 mg/m$^2$ of body surface area, or from about 15 mg/m$^2$ to about 30 mg/m$^2$ of body surface area. In some embodiments, a single dose of Plinabulin or other therapeutic agent may be from about 13.5 mg/m$^2$ to about 30 mg/m$^2$ of body surface area. In some embodiments, a single dose of Plinabulin or other therapeutic agent may be about 5 mg/m$^2$, about 10 mg/m$^2$, about 12.5 mg/m$^2$, about 13.5 mg/m$^2$, about 15 mg/m$^2$, about 17.5 mg/m$^2$, about 20 mg/m$^2$, about 22.5 mg/m$^2$, about 25 mg/m$^2$, about 27.5 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, or about 100 mg/m$^2$, of body surface area.

In some embodiments, a single dose of Plinabulin or other therapeutic agent may be from about 5 mg to about 300 mg, from about 5 mg to about 200 mg, from about 7.5 mg to about 200 mg, from about 10 mg to about 100 mg, from about 15 mg to about 100 mg, from about 20 mg to about 100 mg, from about 30 mg to about 100 mg, from about 40 mg to about 100 mg, from about 10 mg to about 80 mg, from about 15 mg to about 80 mg, from about 20 mg to about 80 mg, from about 30 mg to about 80 mg, from about 40 mg to about 80 mg, from about 10 mg to about 60 mg, from about 15 mg to about 60 mg, from about 20 mg to about 60 mg, from about 30 mg to about 60 mg, or from about 40 mg to about 60 mg, In some embodiments, a single dose of Plinabulin or other therapeutic agent may be from about 20 mg to about 60 mg, from about 27 mg to about 60 mg, from about 20 mg to about 45 mg, or from about 27 mg to about 45 mg. In some embodiments, a single dose of Plinabulin or other therapeutic agent may be about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

The administration period can be a multi-week treatment cycle as long as the tumor remains under control and the regimen is clinically tolerated. In some embodiments, a single dosage of Plinabulin or other therapeutic agent can be administered once a week, and preferably once on each of day 1 and day 8 of a three-week (21 day) treatment cycle. In some embodiments, a single dosage of Plinabulin or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

The treatment cycle can be repeated as long as the regimen is clinically tolerated. In some embodiments, the treatment cycle is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

In some embodiments, the compositions described herein can be used in combination with other therapeutic agents. In some embodiments, the compositions described herein can be administered or used in combination with treatments such as chemotherapy, radiation, and biologic therapies.

Methods of Treatment

Some embodiments relate to a method of treating a brain tumor, the method comprising administering an effective amount of Plinabulin to a subject in need thereof.

In some embodiments, the brain tumor can be selected from metastatic brain tumor, anaplastic astrocytoma, glioblastoma multiforme, oligodendroglioma, ependymomas, meningioma, mixed glioma, and a combination thereof. In some embodiments, the brain tumor is a glioblastoma multiforme. In some embodiments, the brain tumor is a metastatic brain tumor.

In some embodiments, the brain tumor can be selected from Anaplastic astrocytoma, Central neurocytoma, Choroid plexus carcinoma, Choroid plexus papilloma, Choroid plexus tumor, Dysembryoplastic neuroepithelial tumor, Ependymal tumor, Fibrillary astrocytoma, Giant-cell glioblastoma, Glioblastoma multiforme, Gliomatosis cerebri, Gliosarcoma, Hemangiopericytoma, Medulloblastoma, Medulloepithelioma, Meningeal carcinomatosis, Neuroblastoma, Neurocytoma, Oligoastrocytoma, Oligodendroglioma, Optic nerve sheath meningioma, Pediatric ependymoma, Pilocytic astrocytoma, Pinealoblastoma, Pineocytoma, Pleomorphic anaplastic neuroblastoma, Pleomorphic xanthoastrocytoma, Primary central nervous system lymphoma, Sphenoid wing meningioma, Subependymal giant cell astrocytoma, Subependymoma, central nervous system myeloma, and Trilateral retinoblastoma.

In some embodiments, the method described herein can include administering an additional therapeutic agent. In some embodiments, the additional therapeutic agent can be temozolomide, bevicizumab, everolimus, carmustine, lomustine, procarbazine, vincristine, irinotecan, cisplatin, carboplatin, methatrexate, etoposide, vinblasatine, bleomycin, actinomycin, cyclophosphamide, or ifosfamide. In some embodiments, the additional therapeutic agent can be temozolomide. In some embodiments, the additional therapeutic agent can be lomustine.

In some embodiments, the method described herein can further include subjecting the subject to a radiation therapy. In some embodiments, the radiation therapy can be a whole-brain irradiation, fractionated radiotherapy, and radiosurgery.

In some embodiments, the brain tumor is characterized by expression of a mutant form of KRAS. In some embodiments, the brain tumor is characterized by expression of a mutant gene that is not KRAS.

In some embodiments, the method described herein can further include identifying a patient having a cancer characterized by expression of a mutant type of KRAS. In some embodiments, the method described herein can further include identifying a patient having a cancer characterized by expression of a wild type of KRAS. In some embodiments, identifying a patient can include determining whether the patient has a KRAS mutation. Some embodiments relate to a method for treating cancer in a patient identified as having a KRAS mutation, the method comprising administering to the patient a pharmaceutically effective amount of Plinabulin, wherein the patient has been identified by (i) collecting a sample from the patient; (ii) isolating DNA from the sample; (iii) amplifying a KRAS gene or fragment thereof in the isolated DNA; and (iv) detecting whether there is a mutation in the amplified KRAS gene, thereby determining whether the patient has a cancer characterized by a KRAS mutation.

Some embodiments relate to a method of inhibiting proliferation of a brain tumor cell, the method including contacting the brain tumor cell with Plinabulin. In some embodiments, the contacting comprises administering an effective amount of Plinabulin to a subject having the brain tumor cell. In some embodiments, the brain tumor is a glioblastoma multiforme.

Some embodiments relate to a method of inducing apoptosis in a brain tumor cell, the method including contacting the brain tumor cell with Plinabulin. In some embodiments, the contacting comprises administering an effective amount of Plinabulin to a subject having the brain tumor cell. In some embodiments, the brain tumor is a glioblastoma multiforme.

Some embodiments relate to a method of inhibiting progression of brain tumor, the method including administering an effective amount of Plinabulin to a subject in need thereof.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Example 1

The mouse model of glioma used was a PDGF-driven GEMM of glioma that mimics the proneural molecular subgroup of glioblastoma (GBM). This model was based on somatic cell-specific gene transfer; the replication-competent ALV-splice acceptor (RCAS) retroviral system allowed the instillation of particular genetic alterations within tightly regulated windows of differentiation in a cell type-specific manner. The RCAS/tv-a system employed the RCAS retroviral vector to infect mice genetically engineered to express the RCAS receptor (tv-a) in specific cell populations. Here, gliomas were generated by RCAS-mediated transfer of PDGF to nestin-expressing cells in the brain. Nestin was expressed in a stem/progenitor cell population in the brain, and has been demonstrated to be a marker for cancer stem cells located in perivascular regions (PVN) in both human and mouse brain tumors. PDGF-driven gliomas arose with complete penetrance when combined with Ink4a-arf−/− deletion by 4-5 weeks post-infection. These tumors closely mimicked the "proneural" subtype of GBM, in which CDKN2A (encoding for both p16INK4A and p14ARF) deletion was observed in 56% of "proneural" human gliomas. The tumor cell structures that define human gliomas, such as Scherer structures, microvascular proliferation and pseudopalisading necrosis were recreated in this GEMM as shown in FIGS. 1a-1d. Specifically, FIG. 1a shows T2 MRI images of a human GBM display peritumoral edema; FIG. 1b shows T2 MRI images of mouse GBM display peritumoral edema; FIG. 1c shows human micrograph images of H&E stains of a GBM having hallmark pseudopalisading necrosis and microvascular proliferation; and FIG. 1d showed mouse micrograph images of H&E stains of a GBM having hallmark pseudopalisading necrosis and microvascular proliferation.

Glioma cells migrated along white matter tracks, surrounded neurons and blood vessels and accumulated at the edge of the brain in the sub-pial space. In this regard, PDGF-driven GEMMs of glioma closely resembles PVN-GBM, and represents an excellent experimental system to define the interactions between tumor cells and non-neoplastic cells in the tumor microenvironment.

Figure 2B:
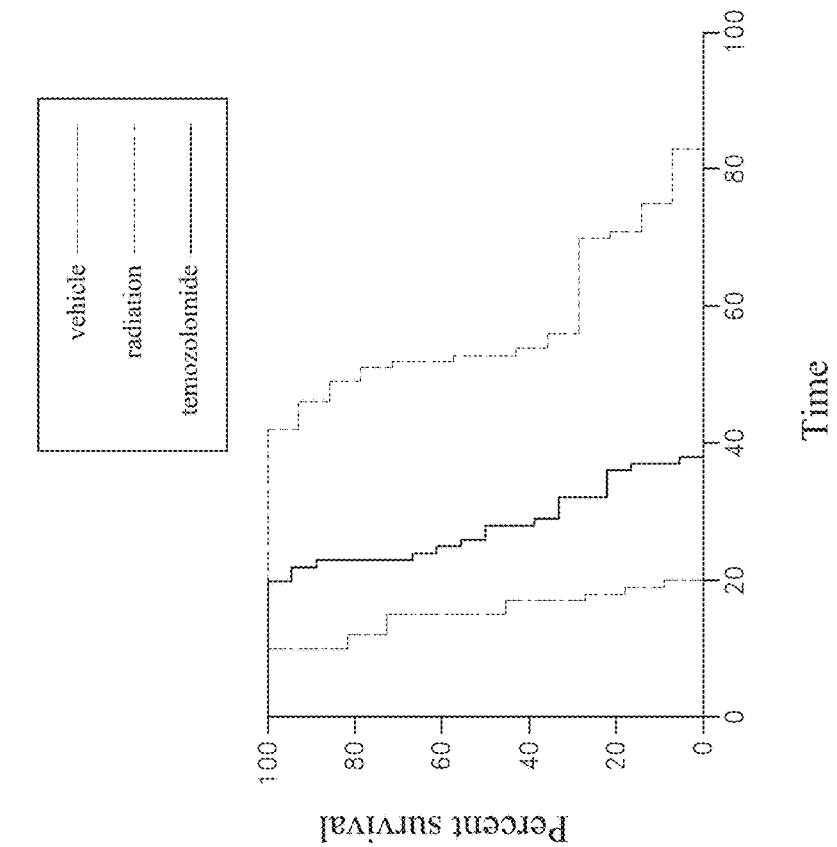
FIGS. 2A and 2B show the T2 weighted MRI images.
Figure 2A:
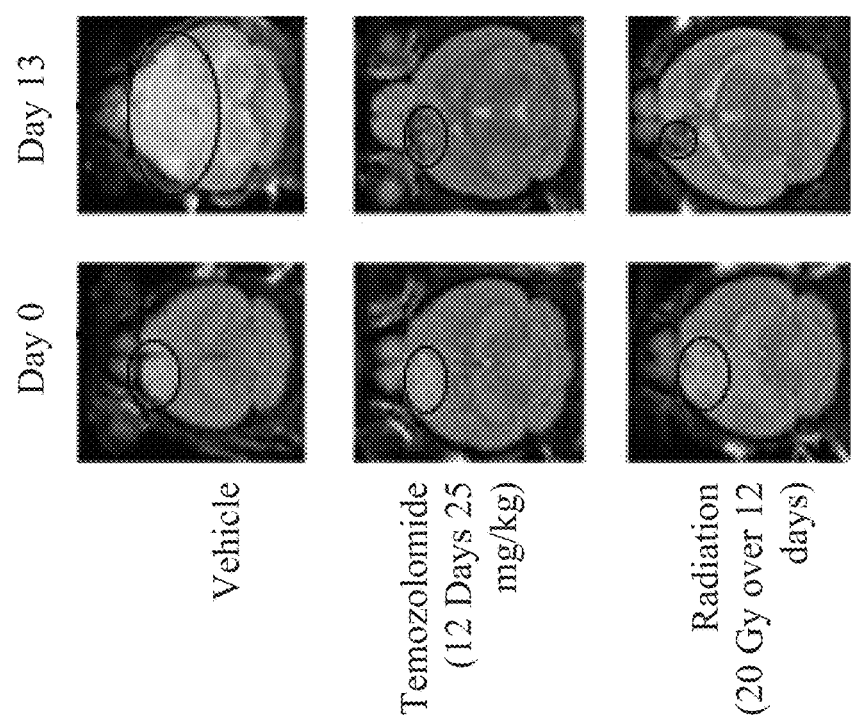

The PDGF-induced model of glioma was used to determine response to radiation and temozolomide as shown in FIGS. 2A and 2B. FIG. 2A shows tumor size of mice with PDGF-induced gliomas treated with vehicle, temozolomide or fractionated radiation; and FIG. 2B shows the survival rate of mice with PDGF-induced gliomas treated with vehicle, temozolomide or fractionated radiation.

Glioma-bearing mice were identified by symptoms and verified by T2 weighted MRI. These mice were either treated with vehicle, temozolomide at 25 mg/kg daily for 12 days, or fractionated radiation at a dose of 2Gy per day 5 days per week for 2 weeks (20Gy total). The two top images in FIG. 2A showed the growth of tumors that were untreated (vehicle), and in contrast, both the temozolomide treated and irradiated tumors shrank in volume over that same period of time. These tumors recurred after treatment and all animals died of recurrent tumor as can be seen in the survival curves for these corresponding cohorts of mice. The data illustrated that: 1) trials were performed in this mouse model, 2) the effect of these treatments on mouse survival mirrored the human condition, 3) all the mice died of disease, and 4) the relatively homogenous outcomes of these murine cohorts supported the use of this experimental paradigm to detect survival differences in the present study.

Mice with PDGF-induced gliomas using RCAS/tv-a were generated. The mice were transgenic for expression of the RCAS receptor (tv-a) from the nestin promoter and having a background of ink4a/arf−/− and lox-stop-lox luciferase, were infected with RCAS-PDGF, or the combination of RCAS-PDGF and RCAS-KRAS that expressed G12D mutant KRAS. The resultant tumors occurred within the first 4-5 weeks in this background for PDGF alone, and about a week shorter for the tumors arising from the combination of PDGF and RCAS. The tumors had the histological characteristics of GBM and were identified by symptoms of lethargy and poor grooming, MRI scans using a T2 weighted sequence, or bioluminescence imaging with an IVIS system. For radiation therapy, mice were treated with 10Gy per day cranially for a single dose. This treatment extended the median survival of cohorts of GBM bearing mice approximately 3 weeks as shown in FIG. 2B. These treated mice began to gain weight and show improved symptoms within a few days, and their MRI imaging characteristics showed stabilization or shrinking of tumor size, and then recurrence and death.

Plinabulin was tested on mice with PDGF-induced gliomas that expressed G12D mutant KRAS. 4-6 week old nestin-tv-a/ink4a-arf−/− mice were anesthetized with Isoflurane and injected with Df-1 cells transfected RCAS-PDGF-B-HA, RCAS-KRAS. Mice were injected with one microliter of a 1:1 mixture of $2\times10^5$ RCAS-PDGF-B-HA/RCAS-KRAS using a stereotactic frame via a 26-gauge needle attached to a Hamilton syringe. Cells were injected into the right frontal cortex, coordinates bregma 1.75 mm, Lat −0.5 mm, and a depth of 2 mm. Mice were monitored carefully for weight loss and put on the study when they lost >0.3 grams total over 2 consecutive days or displayed outward signs of a tumor. In the KRAS group, mice were injected with Plinabulin 7.5 mg/kg i.p. twice per week for 10 weeks. In the control group, mice that were injected with Plinabulin diluent only (40% wt Kolliphor and 60% wt propylene glycol). The mice were monitored for lethargy, hunched posture, appetite loss, outward signs of tumor growth, agitation, weight-loss and overall failure to thrive. The mice were sacrificed when they lost more than 20% of their body weight, mobility, inability to feed or weighed less than 14 grams for a male/12 grams for a female. The mice were sacrificed using $CO_2$; brains were harvested and stored overnight in 10% Neutral buffered formalin and then replaced with Flex 80 and stored at 4 degrees.

Figure 3:
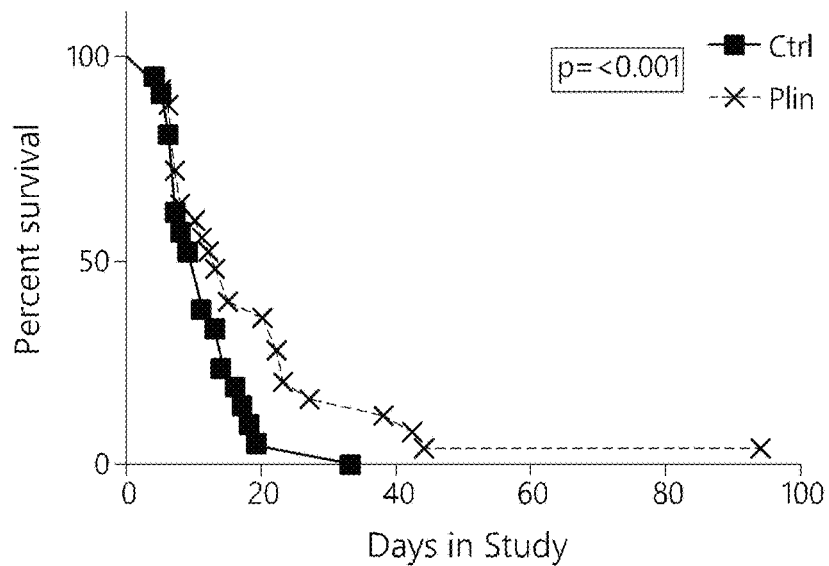
FIG. 3 shows the survival rate of mice with glioblastoma tumor that were treated with control and Plinabulin.

FIG. 3 shows the survival rate of mice with Glioblastoma with the G12D Kras mutation. As shown in FIG. 3, mice having the PDGF-induced model of Glioblastoma generally had a significantly better survival rate in the Plinabulin treated group as compared to the control group (p=0.001).

Example 2

Mice with PDGF-induced gliomas that expressed G12D mutant KRAS were prepared using the procedures according to Example 1 and used in this experiment. 4-6 week old nestin-tv-a/ink4a-arf−/− mice were anesthetized with Isoflurane and injected with Df-1 cells transfected RCAS-PDGF-B-HA, RCAS-KRAS. Mice were injected with one microliter of a 1:1 mixture of $2\times10^5$ RCAS-PDGF-B-HA/RCAS-KRAS using a stereotactic frame via a 26-gauge needle attached to a Hamilton syringe. Cells were injected into the right frontal cortex, coordinates bregma 1.75 mm, Lat −0.5 mm, and a depth of 2 mm. Mice were monitored carefully for weight loss and put on the study when they lost >0.3 grams total over 2 consecutive days or displayed outward signs of a tumor.

Figure 4:
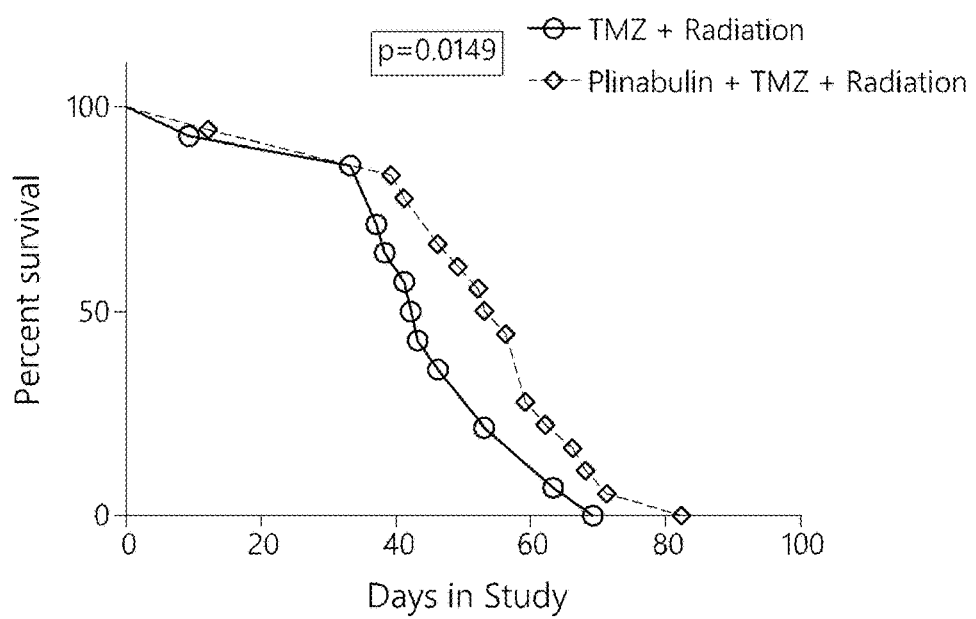
FIG. 4 shows the survival rate of mice with PDGF-induced gliomas characterized by expression of KRAS mutation that were treated with the combination of plinabulin, temozolomide, and radiation and the combination of temozolomide and radiation.

The mice were entered into two study groups. One group was treated with the combination of temozolomide (TMZ), Radiation and Plinabulin: radiation was given at 10gy×1, TMZ and Plinabulin 7.5 mg/kg in Plinabulin diluent was administered intraperitoneally twice a week on Monday and Thursday for 10 weeks. The other group, the control group, was treated with the combination of TMZ and radiation: radiation was given at 10gy×1, TMZ was administered intraperitoneally twice a week on Monday and Thursday for 10 weeks. the mice were monitored for lethargy, hunched posture, appetite loss, outward signs of tumor growth, agitation, weight-loss and overall failure to thrive. The mice were sacrificed when they lost more than 20% of their body weight, mobility, inability to feed or weighed less than 14 grams for a male/12 grams for a female. The mice were sacrificed using $CO_2$; brains were harvested and stored O/N in 10% Neutral buffered formalin and then replaced with Flex 80 and stored at 4 degrees. As shown in FIG. 4, the mice having the PDGF-induced model of Glioblastoma generally had significantly better survival rate in the Plinabulin plus TMZ plus radiation treated group as compared to the control group that received TMZ plus radiation (p=0.0149).

What is claimed is:

1. A method of therapeutically treating a brain tumor comprising administering an effective amount of plinabulin to a subject in need thereof, with the proviso that the brain tumor is not hemangiopericytoma.

2. The method of claim 1, wherein the brain tumor is selected from metastatic brain tumor, anaplastic astrocytoma, Central neurocytoma, Choroid plexus carcinoma, Choroid plexus papilloma, Choroid plexus tumor, Dysembryoplastic neuroepithelial tumor, Ependymal tumor, Fibrillary astrocytoma, Giant-cell glioblastoma, Glioblastoma multiforme, Gliomatosis cerebri, Gliosarcoma, Medulloblastoma, Medulloepithelioma, Meningeal carcinomatosis, Neuroblastoma, Neurocytoma, Oligoastrocytoma, Oligodendroglioma, Optic nerve sheath meningioma, Pediatric ependymoma, Pilocytic astrocytoma, Pinealoblastoma, Pineocytoma, Pleomorphic anaplastic neuroblastoma, Pleomorphic xanthoastrocytoma, Primary central nervous system lymphoma, Sphenoid wing meningioma, Subependymal giant cell astrocytoma, Subependymoma, central nervous system myeloma, and Trilateral retinoblastoma.

3. The method of claim 1, wherein the brain tumor is metastatic brain tumor, anaplastic astrocytoma, glioblastoma multiforme, oligodendroglioma, ependymomas, or a combination thereof.

4. The method of claim 1, wherein the brain tumor is a glioblastoma multiforme.

5. The method of claim 1, wherein the brain tumor is a metastatic brain tumor.

6. The method of claim 1, further comprising administering an additional therapeutic agent.

7. The method of claim 6, wherein the additional therapeutic agent is selected from the group consisting of temozolomide, bevicizumab, everolimus, carmustine, lomustine, procarbazine, vincristine, irinotecan, cisplatin, carboplatin, methatrexate, etoposide, vinblasatine, bleomycin, actinomycin, cyclophosphamide, and ifosfamide.

8. The method of claim 6, wherein the additional therapeutic agent is temozolomide.

9. The method of claim 6, wherein the additional therapeutic agent is a chemotherapeutic agent.

10. The method of claim 1, further comprising subjecting the subject to radiation therapy.

11. The method of claim 10, wherein the radiation therapy is selected from whole-brain irradiation, fractionated radiotherapy, radio surgery, and a combination thereof.

12. The method of claim 1, wherein the brain tumor is characterized by expression of a mutant form of KRAS.

13. The method of claim 1, wherein a single dose of plinabulin is in the range of 5 mg/m$^2$ to about 150 mg/m$^2$ of body surface area.

14. The method of claim 1, wherein a single dose of plinabulin is in the range of 10 mg/m$^2$ to about 30 mg/m$^2$ of body surface area.

15. The method of claim 1, wherein the plinabulin is administered parenterally.

16. A method of inhibiting proliferation of brain tumor cell, comprising contacting the brain tumor cell with Plinabulin, with the proviso that the brain tumor is not hemangiopericytoma.

17. The method of claim 16, wherein contacting comprises administering an effective amount of Plinabulin to a subject having the brain tumor cell.

18. A method of inducing apoptosis in brain tumor cell, comprising contacting the brain tumor cell with Plinabulin, with the proviso that the brain tumor is not hemangiopericytoma.

19. The method of claim 18, wherein contacting comprises administering an effective amount of Plinabulin to a subject having the brain tumor cell.

20. A method of inhibiting progression of brain tumor, comprising administering an effective amount of Plinabulin to a subject in need thereof, with the proviso that the brain tumor is not hemangiopericytoma.

* * * * *

UNITED STATES PATENT AND TRADEMARK OFFICE
CERTIFICATE OF CORRECTION

PATENT NO.       : 10,357,491 B2
APPLICATION NO.  : 16/122482
DATED            : July 23, 2019
INVENTOR(S)      : Lan Huang Page 1 of 1

It is certified that error appears in the above-identified patent and that said Letters Patent is hereby corrected as shown below:

On Page 2, Column 1, Item (56), Line 46, under Other Publications, change "Diketopiperazins" to --Diketopiperazines--.

On Page 2, Column 2, Item (56), Line 4, under Other Publications, change "thereapy:" to --therapy:--.

On Page 4, Column 1, Item (56), Line 47, under Other Publications, change "Purifiied" to --Purified--.

In Column 4, Line 33, change "intrapulmonarilly," to --intrapulmonarily,--.

In Column 6, Line 1, change "croscarmelose;" to --croscarmellose;--.

In Column 7, Line 2, after "80" insert --.--.

In Column 9, Line 52, change "bevicizumab," to --bevacizumab,--.

In Column 9, Line 54, change "methatrexate," to --methotrexate,--.

In Column 9, Line 54, change "vinblasatine," to --vinblastine,--.

In Column 12, Line 60, change "the" to --The--.

In Column 13, Line 40, Claim 7, change "bevicizumab," to --bevacizumab,--.

In Column 14, Line 1, Claim 7, change "methatrexate," to --methotrexate,--.

In Column 14, Line 1, Claim 7, change "vinblasatine," to --vinblastine,--.

Signed and Sealed this
Twenty-sixth Day of November, 2019

Andrei Iancu
*Director of the United States Patent and Trademark Office*